(12) United States Patent
Fan et al.

(10) Patent No.: US 11,311,338 B2
(45) Date of Patent: *Apr. 26, 2022

(54) APPARATUS FOR LASER LITHOTRIPSY

(71) Applicant: Gyrus ACMI, Inc., Southborough, MA (US)

(72) Inventors: Tailin Fan, Southborough, MA (US); Kurt G. Shelton, Southborough, MA (US)

(73) Assignee: Gyrus Acmi, Inc., Westborough, MA (US)

(*) Notice: Subject to any disclaimer, the term of this patent is extended or adjusted under 35 U.S.C. 154(b) by 99 days.

This patent is subject to a terminal disclaimer.

(21) Appl. No.: 16/808,491

(22) Filed: Mar. 4, 2020

(65) Prior Publication Data

US 2020/0197094 A1 Jun. 25, 2020

Related U.S. Application Data

(63) Continuation of application No. 16/302,147, filed as application No. PCT/IB2016/052909 on May 18, 2016, now Pat. No. 10,646,276.

(51) Int. Cl.
A61B 18/16 (2006.01)
A61B 18/26 (2006.01)
(Continued)

(52) U.S. Cl.
CPC ............ *A61B 18/26* (2013.01); *A61B 17/221* (2013.01); *A61B 2017/00057* (2013.01);
(Continued)

(58) Field of Classification Search
USPC .......................................................... 606/15
See application file for complete search history.

(56) References Cited

U.S. PATENT DOCUMENTS 4,939,336 A 7/1990 Meyer et al.
5,275,594 A 1/1994 Baker et al.
(Continued)

FOREIGN PATENT DOCUMENTS

CN 101721248 A 6/2010
CN 109152607 A 1/2019
(Continued)

OTHER PUBLICATIONS

"U.S. Appl. No. 16/302,147, Final Office Action dated Nov. 22, 2019", 7 pgs.

(Continued)

*Primary Examiner* — Nicole F Lavert
(74) *Attorney, Agent, or Firm* — Schwegman Lundberg & Woessner, P.A.

(57) ABSTRACT

An apparatus for fragmenting a stone includes an endoscope, a laser fiber, a sheath and a detection feedback system. The endoscope includes a working channel. The working channel is configured to have a retrieval basket inserted therethrough. The sheath may include a first lumen and a second lumen. A first one of the lumen is connected to the endoscope with a shaft of the endoscope extending through the first lumen. A second one of the lumen is spaced from the shaft of the endoscope providing a channel proximate an exterior side of the shaft. The second lumen has the laser fiber inserted therethrough. The detection feedback system is configured to deliver a low energy check pulse from the laser fiber and detect a response, and configured to at least partially control delivery of a high energy laser pulse from the laser fiber to cause the stone to fragment.

21 Claims, 6 Drawing Sheets

(51) Int. Cl.
  *A61B 17/221*  (2006.01)
  *A61B 17/00*  (2006.01)
  *A61B 18/00*  (2006.01)

(52) U.S. Cl.
  CPC .............. *A61B 2017/2212* (2013.01); *A61B 2018/00642* (2013.01); *A61B 2018/00708* (2013.01); *A61B 2018/00732* (2013.01); *A61B 2018/00785* (2013.01); *A61B 2018/00982* (2013.01); *A61B 2218/002* (2013.01)

(56) References Cited

U.S. PATENT DOCUMENTS

| | | | |
|---|---|---|---|
| 6,538,739 | B1 | 3/2003 | Visuri et al. |
| 9,259,231 | B2 | 2/2016 | Navve et al. |
| 9,282,985 | B2 | 3/2016 | Finkman et al. |
| 10,646,276 | B2 | 5/2020 | Fan et al. |
| 2006/0217688 | A1 | 9/2006 | Lai |
| 2007/0299456 | A1 | 12/2007 | Teague |
| 2009/0137952 | A1* | 5/2009 | Ramamurthy ..... A61B 1/00004 604/95.01 |
| 2010/0137846 | A1 | 6/2010 | Desai et al. |
| 2010/0137847 | A1 | 6/2010 | Cecchetti et al. |
| 2012/0136207 | A1* | 5/2012 | Goldfarb ............ A61B 1/00126 600/106 |
| 2013/0123304 | A1 | 5/2013 | Moore, II et al. |
| 2013/0274712 | A1* | 10/2013 | Schecter ............... A61B 18/02 604/510 |
| 2015/0133728 | A1 | 5/2015 | Finkman et al. |
| 2019/0282299 | A1 | 9/2019 | Fan et al. |

FOREIGN PATENT DOCUMENTS

| | | |
|---|---|---|
| CN | 109152607 B | 4/2020 |
| CN | 111281532 A | 6/2020 |
| DE | 102011109069 A1 | 1/2013 |
| EP | 3439570 A1 | 2/2019 |
| EP | 3439570 B1 | 12/2019 |
| EP | 3632359 A1 | 4/2020 |
| JP | H03111039 A | 5/1991 |
| JP | H0417847 A | 1/1992 |
| JP | 1279595 A | 1/2001 |
| JP | 2017515561 A | 6/2017 |
| JP | 2019522505 A | 8/2019 |
| JP | 6672479 B2 | 3/2020 |
| JP | 2020078705 A | 5/2020 |
| JP | 6942831 B2 | 9/2021 |
| WO | WO-9307806 A1 | 4/1993 |
| WO | WO-2004049928 A1 | 6/2004 |
| WO | WO-2013123304 A1 | 8/2013 |
| WO | WO-2016049160 A1 | 3/2016 |
| WO | WO-2017199066 A1 | 11/2017 |

OTHER PUBLICATIONS

"U.S. Appl. No. 16/302,147, Non Final Office Action dated Sep. 26, 2019", 8 pgs.
"U.S. Appl. No. 16/302,147, Notice of Allowance dated Feb. 6, 2020", 7 pgs.
"U.S. Appl. No. 16/302,147, Preliminary Amendment filed Nov. 16, 2018", 7 pgs.
"U.S. Appl. No. 16/302,147, Response filed Jan. 6, 2020 to Final Office Action dated Nov. 22, 2019", 10 pgs.
"U.S. Appl. No. 16/302,147, Response filed Nov. 5, 2019 to Non Final Office Action dated Sep. 26, 2019", 13 pgs.
"Chinese Application Serial No. 201680085793.9, Office Action dated Mar. 29, 2019", with English translation, 9 pgs.
"Chinese Application Serial No. 201680085793.9, Office Action dated Jul. 29, 2019", with English translation, 8 pgs.
"Chinese Application Serial No. 201680085793.9, Response filed Jun. 5, 2019 to Office Action dated Mar. 29, 2019", with machine translation, 18 pgs.
"Chinese Application Serial No. 201680085793.9, Response filed Oct. 9, 2019 to Office Action dated Jul. 29, 2019", with machine translation, 9 pgs.
"European Application Serial No. 16726960.4, Communication Pursuant to Article 94(3) EPC dated Feb. 19, 2019", 5 pgs.
"European Application Serial No. 16726960.4, Intention to Grant dated Sep. 30, 2019", 37 pgs.
"European Application Serial No. 16726960.4, Response filed May 31, 2019 to Communication Pursuant to Article 94(3) EPC dated Feb. 19, 2019", 52 pgs.
"European Application Serial No. 19204014.5, Communication Pursuant to Article 94(3) EPC dated Nov. 10, 2020", 5 pgs.
"European Application Serial No. 19204014.5, Extended European Search Report dated Feb. 25, 2020", 5 pgs.
"European Application Serial No. 19204014.5, Response filed Aug. 8, 2020 to Extended European Search Report dated Feb. 25, 2020", 1 pg.
"International Application Serial No. PCT/IB2016/052909, International Preliminary Report on Patentability dated Nov. 29, 2018", 6 pgs.
"International Application Serial No. PCT/IB2016/052909, International Search Report dated Jan. 25, 2017", 3 pgs.
"International Application Serial No. PCT/IB2016/052909. Written Opinion dated Jan. 25, 2017", 4 pgs.
"Japanese Application Serial No. 2018-558356, Notification of Reasons for Refusal dated Apr. 11, 2019", with English translation, 6 pgs.
"Japanese Application Serial No. 2018-558356, Notification of Reasons for Refusal dated Jul. 29, 2019", English translation, 7 pgs.
"Japanese Application Serial No. 2018-558356, Notification of Reasons for Refusal dated Nov. 26, 2019", with English translation, 7 pgs.
"Japanese Application Serial No. 2018-558356, Response filed Jan. 16, 2020 to Notification of Reasons for Refusal dated Nov. 26, 2019", with English translation, 8 pgs.
"Japanese Application Serial No. 2018-558356, Response filed Jul. 22, 2019 to Notification of Reasons for Refusal dated Apr. 11, 2019", with English translation, 10 pgs.
"Japanese Application Serial No. 2018-558356, Response filed Nov. 19, 2019 to Notification of Reasons for Refusal dated Jul. 29, 2019", with English translation, 14 pgs.
"European Application Serial No. 19204014.5, Response Filed Mar. 10, 2021 to Communication Pursuant to Article 94(3) EPC dated Nov. 10, 2020", 10 pgs.
"Japanese Application Serial No. 2020-035787, Notification of Reasons for Refusal dated Mar. 22, 2021", with English translation, 11 pgs.
"Japanese Application Serial No. 2020-035787, Response filed Jun. 9, 2021 to Notification of Reasons for Refusal dated Mar. 22, 2021", w/ English Claims, 7 pgs.
U.S. Appl. No. 16/302,147 U.S. Pat. No. 10,646,276, filed Nov. 16, 2018, Apparatus for Laser Lithotripsy.

\* cited by examiner

APPARATUS FOR LASER LITHOTRIPSY

CROSS REFERENCE TO RELATED APPLICATIONS

This patent application is a continuation application of issued application Ser. No. 16/302,147 filed Nov. 16, 2018, now U.S. Pat. No. 10,646,276, which is a U.S. National Stage application of International Patent Application Number PCT/IB2016/052909 filed May 18, 2016, which are hereby incorporated by reference in their entireties.

BACKGROUND

Technical Field

The exemplary and non-limiting embodiments relate generally to laser lithotripsy and, more particularly, to an apparatus and method for laser lithotripsy.

Brief Description of Prior Developments

U.S. Pat. No. 9,282,985 describes aiming beam detection for laser lithotripsy. U.S. Pat. No. 9,259,231 describes computer aided image-based lithotripsy. U.S. Patent Publication No. 2006/0217688 A1 describes use of a low energy laser pulse and an amplified laser pulse.

SUMMARY

The following summary is merely intended to be exemplary. The summary is not intended to limit the scope of the claims.

In accordance with one aspect, an example embodiment is provided in an apparatus for fragmenting a stone, the apparatus comprising an endoscope comprising a working channel, where the working channel is configured to have a retrieval basket inserted therethrough; a laser fiber; a sheath comprising at least two lumen, where a first one of the lumen is connected to the endoscope with a shaft of the endoscope extending through the first lumen, where a second one of the lumen is spaced from the shaft of the endoscope providing a channel proximate an exterior side of the shaft, where the second lumen has the laser fiber inserted therethrough; and a detection feedback system configured to deliver a low energy check pulse from the laser fiber and detect a response based upon the low energy check pulse, and configured to at least partially control delivery of a high energy laser pulse from the laser fiber to cause the stone to fragment.

In accordance with another aspect, an example method comprises connecting a sheath to a shaft of an endoscope, where the sheath comprises at least two lumen, where a first one of the lumen is connected to the endoscope with the shaft of the endoscope extending through the first lumen, and where a second one of the lumen is spaced from the shaft of the endoscope providing a channel proximate an exterior side of the shaft; inserting a laser fiber into the second lumen; and controlling delivery of energy from the laser fiber comprising a low energy check pulse from the laser fiber for detecting a response based upon the low energy check pulse, and a high energy laser pulse from the laser fiber for causing a stone to fragment.

In accordance with another aspect, an example embodiment is provided in a non-transitory program storage device readable by a machine, tangibly embodying a program of instructions executable by the machine for performing operations, the operations comprising: deliver a low energy check pulse from a laser fiber; detecting a response based upon the low energy check pulse; and based, at least partially, upon the detected response, determining to: deliver a high energy laser pulse from the laser fiber to cause a stone to fragment, or deliver another low energy check pulse from the laser fiber.

BRIEF DESCRIPTION OF THE DRAWINGS

The foregoing aspects and other features are explained in the following description, taken in connection with the accompanying drawings, wherein.

DETAILED DESCRIPTION OF EMBODIMENTS

Figure 1:
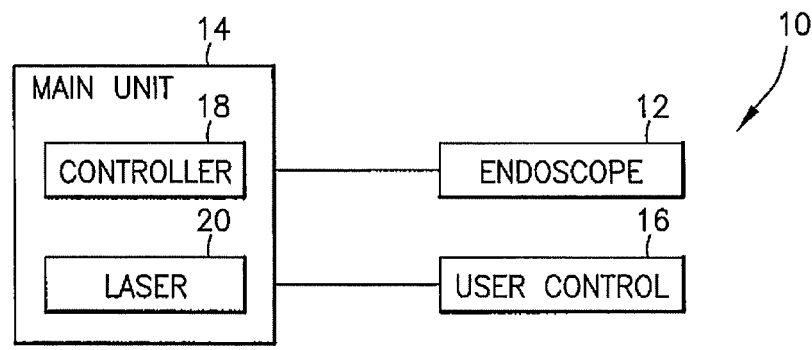
FIG. 1 is a block diagram illustrating an example embodiment.

Referring to FIG. 1, there is shown block diagram of an apparatus 10 incorporating features of an example embodiment. Although the features will be described with reference to the example embodiments shown in the drawings, it should be understood that features can be embodied in many alternate forms of embodiments. In addition, any suitable size, shape or type of elements or materials could be used.

Figure 2:
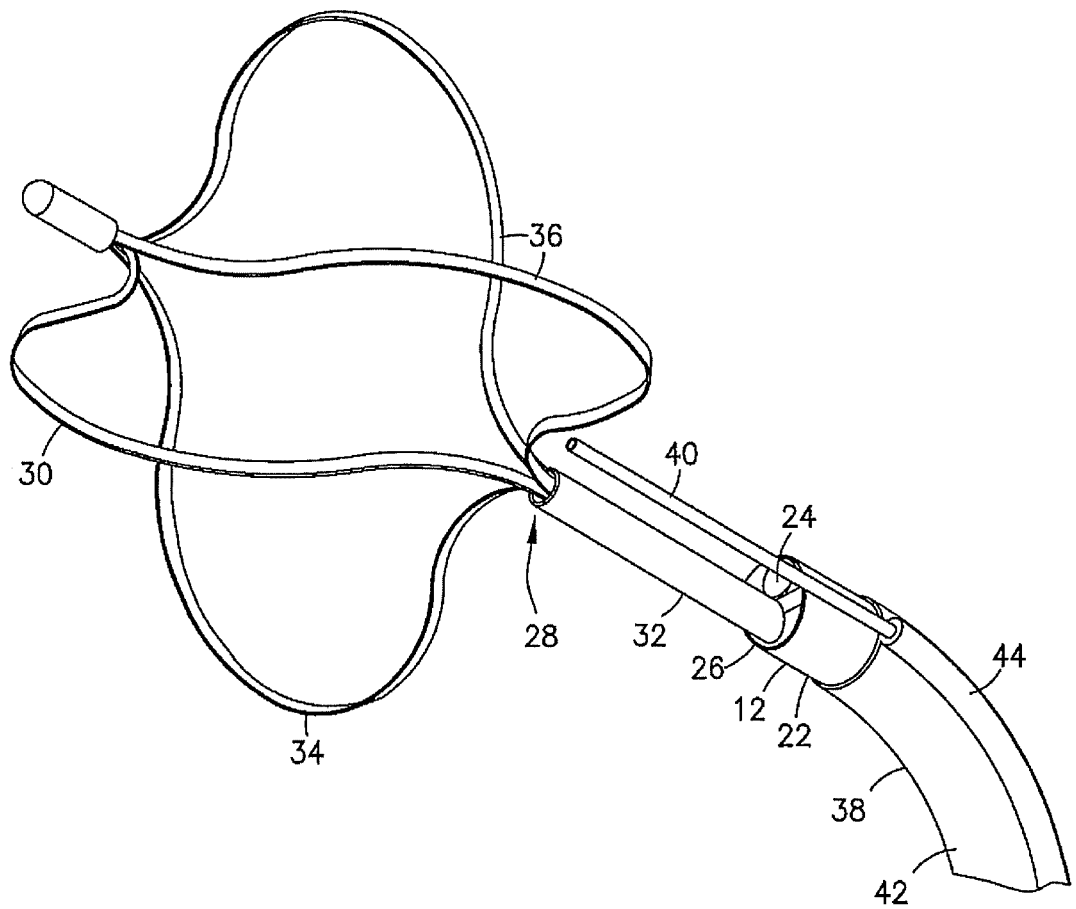
FIG. 2 is a partial perspective view illustrating a proximal end of the endoscope shown in FIG. 1.

The apparatus 10 in this example embodiment is adapted to be used for laser lithotripsy. The apparatus 10 comprises an endoscope 12, a main unit 14 and a user control 16. The user control 16 may be a foot pedal for example. The user control 16 may be used by the user to control delivery of a laser pulse from a laser 20 for example. The main unit 14 may comprise multiple devices; perhaps provided as separate units. The main unit comprises a controller 18 and the laser 20. The laser 20 may comprise more than one laser. Referring also to FIG. 2, the endoscope 12 comprises a shaft 22 having an objective head for an optical image fiber or bundle 24, and a working channel 26. The distal end of the shaft 22 is controllably deflectable by the user at a proximal end of the endoscope.

FIG. 2 shows a tool 28 extending out of a distal end of the working channel 26. The tool 28 may be a Surgeon Controlled Basket Device (SCBD). The tool 28 is removably inserted into the working channel 26 at the proximal end of the endoscope 12 and generally comprises a basket device 30 and a sheath 32. The basket device 30 comprises an elongate shaft which extends through the sheath 32 and a front end basket 34. The basket 34 comprises arms 36. The basket 34 has a first position inside the sheath 32 and a second position extended from the front end of the sheath 32. In the first position the arms 36 are resiliently compacted relative to each other inside the sheath 32. FIG. 2 shows the second position where the arms 36 have resiliently expanded when no longer constrained by the sheath 32. In the second position, the basket 34 may be moved over a stone and then collapsed (by moving the basket device 30 and the sheath 32 relative to one another) for the basket 34 to grasp onto the stone. In alternate examples, means other than a Surgeon Controlled Basket Device (SCBD) may be used to temporarily fix a stone for lithotripsy, such as a gel for example.

Figure 3:
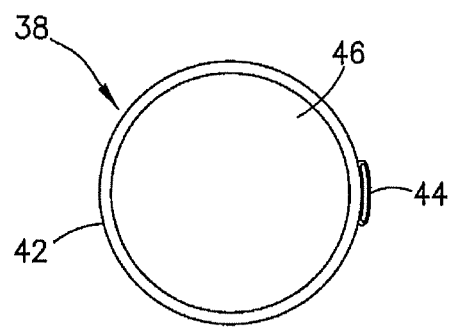
FIG. 3 is a sectional view illustrating the sheath attached to the endoscope shown in FIG. 2.
Figure 4:
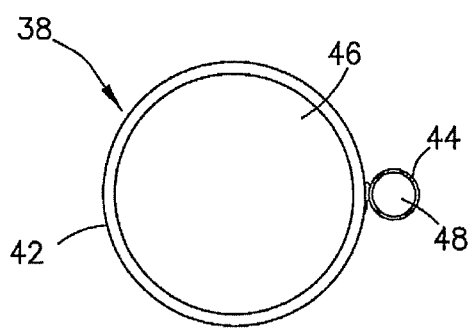
FIG. 4. is a sectional view similar to FIG. 3 showing the collapsed tube in an expanded configuration.

FIG. 2 shows an auxiliary device 38 attached to the shaft 22 of the endoscope 12. The auxiliary device 38 in this example is a sheath configured to support the laser fiber 40 relative to the shaft 22 of the endoscope. The laser fiber 40 is connected to the laser 20 to allow a laser pulse to be delivered through the laser fiber 40 to a location proximate the distal end of the endoscope. Referring also to FIGS. 3-4, the sheath 38 is generally comprised of a soft and resilient material, such as a polymer material for example. The sheath 38 is configured to be slid onto the shaft 22 and may be removed after use for disposal. The sheath 38 generally comprises a first tube 42 and an integrally formed second tube 44. The second tube 44 is smaller than the first tube 42 and runs generally parallel along the exterior side of the first tube 42.

Figure 5:
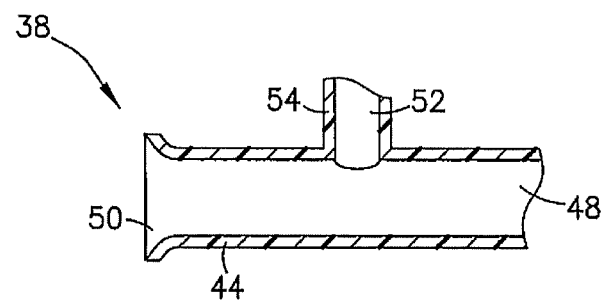
FIG. 5 is a sectional view illustrating the proximal end of the collapsible tube shown in FIGS. 2-4.

FIG. 3 shows the second tube 44 in its natural, home configuration. In this first configuration the second tube 44 has a collapsed state against the exterior side of the first tube 42. The second tube 44 is resiliently expandable from its natural collapsed state to an expanded configuration as shown in FIG. 4. Fluid introduced into the proximal end of the second tube 44 may be used to expand the second tube 44. Thus, with the second tube 44 expanded, the sheath 38 comprises a first lumen 46 for the shaft 22 of the endoscope and a second lumen 48 for insertion of the laser fiber 40; to guide the laser fiber to a location proximate the distal end of the shaft 22. Referring also to FIG. 5, a cross sectional view of an example of the proximal end of the second tube 44 is shown. In this example the proximal end of the second tube 44 comprises a laser fiber entry 50 and a separate liquid entry 52 into the second lumen 48. In this example the laser fiber entry 50 is substantially rigid and has a general tapered or funnel shape as a lead-in into the second lumen 48. The liquid entry 52 in this example comprises a post 54 configured to be connected to a source of liquid, such as irrigation liquid. However, in alternate examples, different types of structure(s) could be provided at the proximal end of the second tube 44.

Figure 6:
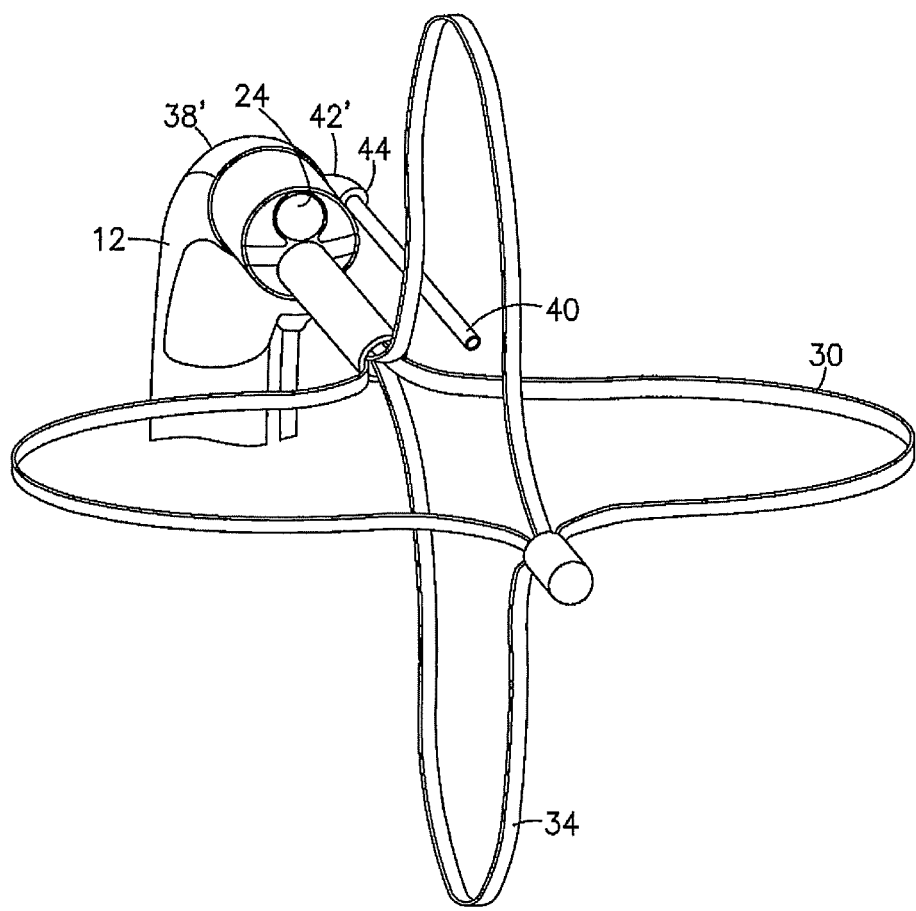
FIG. 6 is a perspective view of an alternate example embodiment.

Referring also to FIG. 6, an alternate example of the sheath 38' is shown. In this example the sheath 38' is shown attached to the endoscope 12 with the basket device 30 deployed and the laser fiber 40 positioned substantially identical to that shown in FIG. 2. However, the sheath 38' comprises a clip 42' which attaches the second tube 44 to the endoscope 12. This illustrates that more than one way may be provided to removably connect the laser fiber sheath to the endoscope. In another alternate example the laser fiber sheath may have the collapsible tube 44 located in the working channel 26. Thus, in the example of when the channel 44 is located in the working channel 26, the portion of the working channel 26 needed for the laser fiber 40 may be substantially free for use for other purposes (such as irrigation for example) while the tube 44 is collapsed. In this alternate example the first tube 42 may or may not be provided with the second tube 44. If the first tube 42 is provided, it may be used to channel a medical tool for example or separate different irrigation flow paths (in/out) for example.

Figure 13A:
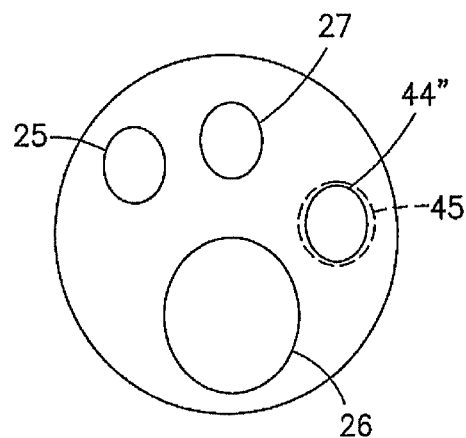
FIGS. 13A and 13B shown schematic examples of an endoscope having features as described herein.
Figure 13B:
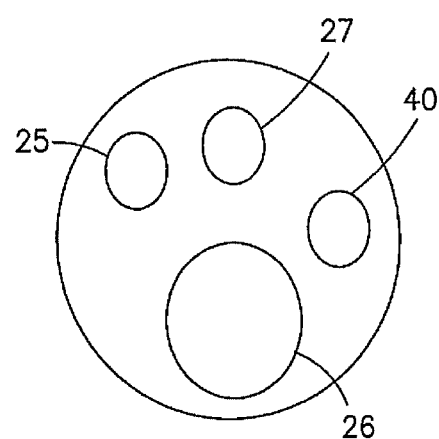

Alternatively, an additional channel outside of the working channel 26 may be integrated into the endoscope itself for either removable passage of a laser or for a fixed laser fiber. One example of this is shown in FIG. 13A where an off-center channel 44" is provided in the endoscope itself, either as a removable passage inside another channel 45 or as a fixed laser channel. Another example of this is shown in FIG. 13B where the endoscope has an off-center fixed laser fiber 40 separate from the image and illumination bundles 25, 27.

In one example Holmium:YAG (Ho:YAG) laser lithotripsy may be used with a laser light of 2170 nm wavelength to break kidney stones of various composition into small pieces by photothermal effect. During this process it is desired to target the stone at a fixed position and to avoid the stone breaking into a few chunks before being reduced to small sizes (pre-mature breaking up). To stabilize the kidney stone during the procedure, some doctors try to retain the stone with basket, and effectively chisel off the stone around the periphery while turning the basket. This is a side-by-side deployment of the basket and laser fiber. In applying such a technique with current flexible endoscopes, the basket and laser fiber go through the same working channel, typically 1.2 mm diameter (3.6 Fr). Together, these two instruments take up most of the working channel lumen. Because of this, they become difficult to operate independently as required by the procedure. The working channel of a flexible endoscope is commonly centrally located along the endoscope body.

By using the basket to hold the stone, one would expect increased fragmentation time efficiency due to reduced stone retropulsion and migration effects. However, it has been found that stone entrapment can result in a decrease in fragmentation time efficiency. The lack of improvement in fragmentation time efficiency with stone entrapment may be due to the inability to effectively maneuver the laser fiber through the working channel shared with the entrapment device. This limitation would be similar to that noted with laser baskets which allow the laser to fire only through the center of the stone. Features as described herein may be used to optimize coupling between the laser fiber and the entrapped stone; to thereby increase time efficiency during a fragmentation procedure.

Another problem with conventional placement of a basket device and a laser fiber in the same endoscope working channel is that the working channel is the'same channel for irrigation fluid (for clearing the visual field and carrying the laser light heat out of the ureter or kidney). The flow of the fluid in the working channel is, therefore, reduced and can become inadequate. The size of the working channel on a flexible endoscope is restricted by the scope shaft diameter and the space taken up by mechanisms inside the endoscope shaft. The shaft diameter is, in turn, restricted by the body cavity the scope is used for. In terms of an ureteroscope in particular, a common ureter access sheath (UAS) is 12-14 Fr for a ureter not pre-stented. The endoscope goes through the access sheath of 4 mm inner diameter (ID). Space has to be left between the UAS ID and the scope shaft, so that the scope can go into the UAS with ease, and the same space is the outflow path for the irrigation water. As examples, GYRUS ACMI DUR-8 Ultra has a shaft outer diameter (OD) 2.9 mm; OLYMPUS URF-P5 has a shaft OD 2.6 mm.

By placing a second circular lumen side-by-side with these endoscopes inside 12-14 Fr UAS, the second lumen can have an OD 1.1 mm for DUR-8 Ultra, or OD 1.4 mm for URF-P5.

To solve the problems, noted above, caused by only one working channel for two instruments, i.e. the basket device and the laser fiber to go through, features as described herein may be used to design a collapsible external flexible tunnel attached to the shaft of flexible endoscope. This tunnel, made of thin flexible polymer material, may be completely collapsed along a majority of its length (perhaps not collapsed at its proximal end) when the endoscope is inserted into the ureter, or through the UAS into the ureter. In the collapsed state, this tunnel adds a minimal thickness to the scope OD on one side and, thus, is not inconvenient for insertion and does not inhibit the insertion. Once the endoscope is deployed and the laser is ready to be introduced into the patient's body lumen such as the ureter for example, the external tunnel can be distended by injection of water into it. Then, the laser fiber can be inserted through the opened tunnel. At the end of insertion, the tip of laser fiber emerges at the endoscope distal end to the side of the scope's shaft.

A typical endoscope has its tip and the segment at the distal end of its shaft to be able to deflect in two opposite directions. For the purpose of description, these two directions are referred to as "up" and "down". When the tip is deflected this way, the middle line along the shaft on the left and right is neutral in terms of shaft bending. Left or right, or both sides, is the ideal location to attach the tunnel, since at the neutral plane an attached extern along tube would not, or minimally, affect the bending of the shaft, since the neutral line is where the length does not change with the bending, thus does not impede the shaft bending. When the laser goes through the externally attached tunnel, the regular working channel is reserved for the basket device and irrigation fluid. Thus, the basket and laser fiber can be manipulated free from mutual interference. When the basket goes through the working channel of the scope and the laser fiber goes through the attached tunnel, these two instruments do not interfere with each other when the surgeon manipulates them independent from each other. The add-on tunnel 44 may extend all the way to the proximal end of the endoscope. At the proximal end of the scope, the add-on tunnel 44 may end at an add-on head block that is attached to the handle of the scope. In this add-on tunnel 44, the laser goes into the tunnel through a port on the add-on head block.

Figure 7:
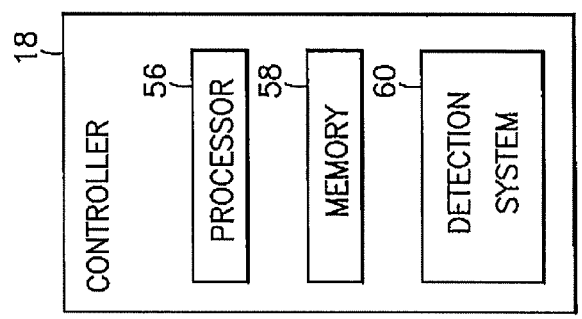
FIG. 7 is a block diagram illustrating some components of the controller shown in FIG. 1.

Referring also to FIG. 7, the controller 18 generally comprises a processor 56 and a memory 58. The controller may be configured to provide various different features; including at least partially controlling delivery of laser pulses from the laser 20 to the laser fiber 40 for example. In this example the controller comprises a detection system 60. The detection system 60 preferably comprises use of at least a portion of the processor 56 and memory 58 with software code. The detection system 60 uses optical information input into the image bundle 24 to detect one or more conditions or situations in front of the objective head of the endoscope. In the example described, the controller 18 is configured to use the detection system to determine if and/or how the laser 20 and laser fiber 40 should be used to deliver a laser pulse. The detection system 60 may also be used as an input for the controller 18 to control at least one other predetermined function or operation.

Figure 8:
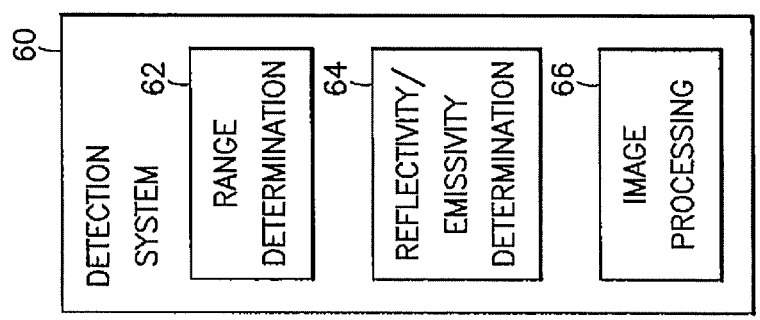
FIG. 8 is a block diagram illustrating some components of the detection system shown in FIG. 7.

Referring also to FIG. 8, the detection system 60 in this example is configured to provide a range determination feature 62, a reflectivity and/or emissivity determination feature 64, and an image processing feature 66. However, in alternate examples more or less features may be provided by the detection system 60. For example, a system could be provided which has the reflectivity and/or emissivity determination feature 64, but not the image processing feature 66. Alternatively, a system could be provided which has the image processing feature 66, but not the reflectivity/emissivity determination feature 64.

The range determination feature 62 is configured to determine a range or distance between the proximal end of the laser fiber 40 and an object in the laser path in front of the laser fiber 40, such as a stone or a portion of one of the arms 36 of the basket 34. The laser fiber 40 may deliver a low energy laser pulse and, based upon a response from this low energy laser pulse, such as sensed as input to the image bundle 24 or back through the laser fiber 40 for example, the detection system may be able to determine the range or distance between the proximal end of the laser fiber 40 and an object in the laser path in front of the laser fiber 40. This may be based upon timing of the response versus the initiation of the laser pulse and/or with use of image processing for example.

The reflectivity and/or emissivity determination feature 64 may be used by the controller 18 to adjust or control delivery of laser pulses from the laser 20 through the laser fiber 40. In one example, the reflectivity and/or emissivity determination feature 64 may be used to prevent, based upon a predetermined condition, a high energy laser pulse from being used.

In a conventional procedure, laser energy is typically applied as a first step and, after a stone is broken down, then a basket is inserted to capture the fragments. However, often there is retropulsion which causes the stone fragment(s) to fly off into a different region(s) of a kidney, such as following a strong laser energy pulse. The surgeon would then need to chase down a stone to apply more energy or to capture and remove the stone fragment(s). Features as described herein may be used to provide the advantage of having a low energy check pulse to determine if it is safe to fire laser energy at a stone. This may be combined with the side firing laser and basket combination described above.

The basket-detect laser feature may use a reflectivity measurement for laser equipment to provide an auto-shutoff of the laser when a basket wire 36 is detected. Alternatively, or additionally, this could be an image processing detection feature that interlocks the laser with the image processor. Laser reflectivity detection may be preferable since it may be less susceptible to slight variances in the image such as blood, bubbles during lithotripsy, laser flash in the image, etc.

By using two different energy laser pulses, the laser pulses may be multiplexed inside the laser equipment for object detection/determination using one type of pulse and laser firing for stone destruction using another different type of pulse. The basket-detect laser feature can also work with a motorized basket rotation for automated stone dusting. Laser settings can be adjusted based on effectiveness by utilizing a laser range finder to assess how effective each laser pulse is on the stone. As one example method, the stone may be moved relative to laser path in the x-y plane, rotate the basket wires, repositioning the stone and the basket combination, and check again with a pulsed laser.

Figure 9:
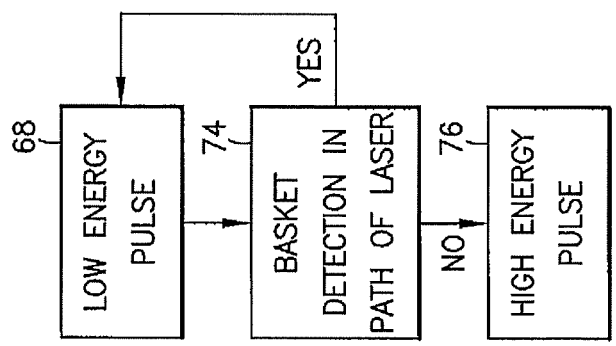
FIG. 9 is a diagram illustrating features of an example method.
Figure 10:
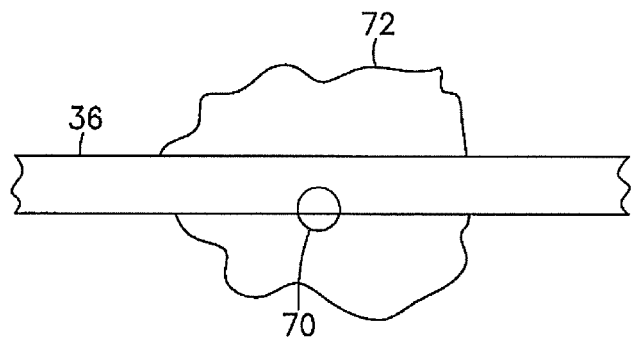
FIG. 10 is a schematic diagram illustrating a stone and a portion of a basket arm in a path of a laser pulse.

Referring to FIG. 9, an example is shown where a low energy pulse is first delivered as indicated by block 68. Referring also to FIG. 10, the detection system 60 may then be used to determine if a portion of the basket, such as arm 36, is in the path 70 of the laser pulse; located in front of the stone 72. As indicated by block 74, if the basket is not detected, the system may allow the high energy pulse to be delivered as indicated by block 76. However, if the basket is detected, the system may prevent the high energy pulse from being delivered. Thus, the low energy check pulse may be used to determine if it is safe to fire the high energy laser pulse. At 74 an interlock signal could be generated to control whether or not the high energy pulse is allowed to fire. This prevents the high energy pulse from damaging the basket arm 36.

Because the basket 34 may be rotated relative to the laser fiber 40, there is a risk that the basket arms 36 may be moved into the path of the laser pulse 70. If the basket arm 36 was damaged by a laser pulse, the damaged basket might be hard to remove from the patient or cause other problems. Thus, by preventing the basket arm 36 from being damaged by the laser pulse, this reduces potential problems based upon basket damage. Features as described herein may be used to provide an auto-shutoff, when the basket is detected in the path 70, to prevent damage to the basket.

Figure 11:
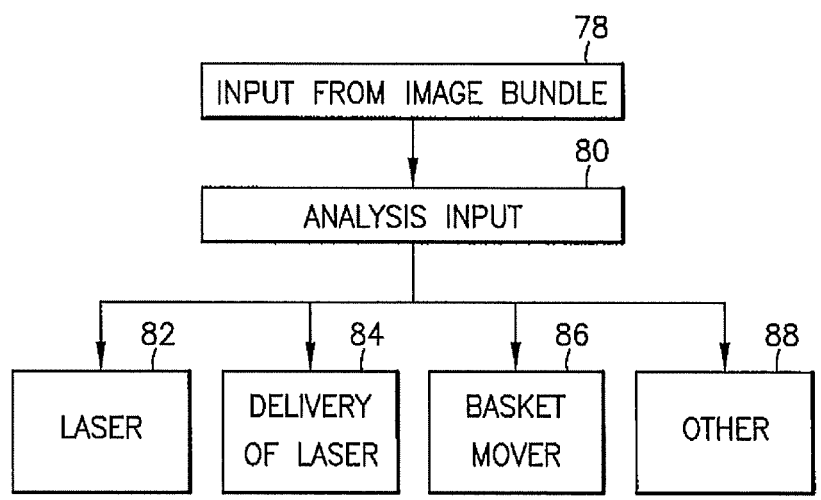
FIG. 11 is a diagram illustration an example method.

Referring also to FIG. 11, features as described herein may use input from the image bundle as indicated by block 78 as input which is analyzed as indicated by block 80. Based upon the analysis of the input, the system may be configured to perform one or more actions including controlling the laser(s) as indicated by 82, controlling delivery of the laser pulses as indicated by 84, using an automatic basket mover 86 to automatically move a basket arm 36 out of the path 70 of the laser pulse, and/or some other action as indicated by 88. The basket mover may rotate the basket 34 to thereby rotate the stone (located in the basket) relative to the path 70 of the laser pulse. Reflectance/emissivity may be measured by multiplexing the low and high energy pulses at any desired rate such as 1:1 or 10:1 for example. Control 82 of the laser may include, for example, changing use of different power settings or frequency or wavelength.

Figure 12:
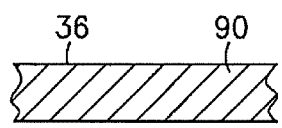
FIG. 12 is a diagram illustrating an image recognition patter provided on the basket arms.

In one type of example, the image processing 66 may use color to distinguish the basket arm 36. For example, the basket arms 36 may have a metallic gray or dark green, or bright yellow or copper color, whereas the stone may have a white or pale yellow color. The color of the basket arms could be multi-colored with a pattern for example. In another example the basket arm 36 may be provided with an indicia or optical pattern 90 as shown by the example in FIG. 12 for faster or better image recognition. The image processing may additionally or alternatively use geometry recognition or boarder recognition or color differentiation between the stone 72 and the basket arm 36 as illustrated by FIG. 10 for example. The range detection feature may be used to help calculate geometry and/or determine the power to be used for the laser pulse. The detection system 60 may also be configured to detect motion of the stone 72 (and fragments) and/or basket 34; individually or perhaps relative to each other for example.

The side firing laser fiber location may be used to hit a stone in an off center location of the stone; to chip away at edges of the stone into smaller fragments. However, if needed, the laser fiber 40 (or an additional laser fiber) may be inserted into the working channel 26 to provide firing at the center region of the stone. Thus, features as described herein allow multiple different locating positions for the laser fiber relative to the endoscope. This provides an endoscope/laser-fiber configuration flexibility which was not available before. Features also allow more than one laser fiber to be deployed with the endoscope at a same time; perhaps firing at a same time for example.

An example apparatus, for fragmenting a stone, may be provided comprising: an endoscope comprising a working channel, where the working channel is configured to have a retrieval basket inserted therethrough; a laser fiber; a sheath comprising at least two lumen, where a first one of the lumen is connected to the endoscope with a shaft of the endoscope extending through the first lumen, where a second one of the lumen is spaced from the shaft of the endoscope providing a channel proximate an exterior side of the shaft, where the second lumen has the laser fiber inserted therethrough; and a detection feedback system configured to deliver a low energy check pulse from the laser fiber and detect a response based upon the low energy check pulse, and configured to at least partially control delivery of a high energy laser pulse from the laser fiber to cause the stone to fragment.

The first lumen may be formed, at least partially, by a first tube, and the second lumen may be formed, at least partially, by a flexible tube configured to collapse against the first-tube. The second lumen may comprise a substantially rigid entrance at a proximal end of the second lumen. A proximal end of the second lumen may comprise both a laser fiber entry and a separate liquid entry into the second lumen. The detection feedback system may comprise a range detection system configured to detect a range between an end of the laser fiber and an object which the low energy check pulse impacts. The detection feedback system may be configured to measure reflectivity and/or emissivity. The detection feedback system may be configured to use image processing. The detection feedback system may be configured to recognize at least one of: a shape of at least a portion of the retrieval basket, a color of at least a portion of the retrieval basket, and a pattern on at least a portion of the retrieval basket. The detection feedback system may be configured to prevent the high energy laser pulse from being delivered based upon the detection feedback system determining that the high energy laser pulse would impact the retrieval basket. The detection feedback system may comprise means for detecting if a portion of the retrieval basket is located in a path in front of the laser fiber.

An example method may comprise: connecting a sheath to a shaft of an endoscope, where the sheath comprises at least two lumen, where a first one of the lumen is connected to the endoscope with the shaft of the endoscope extending through the first lumen, and where a second one of the lumen is spaced from the shaft of the endoscope providing a channel proximate an exterior side of the shaft; inserting a laser fiber into the second lumen; and controlling delivery of energy from the laser fiber comprising a low energy check pulse from the laser fiber for detecting a response based upon the low energy check pulse, and a high energy laser pulse from the laser fiber for causing a stone to fragment.

The method may further comprise, before inserting the laser fiber into the second lumen, inserting a fluid into the second lumen to expand the second lumen from a collapsed configuration to an expanded configuration. The method may further comprise using a range detection system to detect a range between an end of the laser fiber and an object which the low energy check pulse impacts. The method may further comprise using a detection feedback system configured to: measure reflectivity and/or emissivity based upon the low energy check pulse, and/or identify an object in front of a path of the low energy check pulse by image processing.

An example embodiment may be provided in a non-transitory program storage device, such as memory 58 for example, readable by a machine, tangibly embodying a program of instructions executable by the machine for performing operations, the operations comprising: delivering a low energy check pulse from a laser fiber; detecting a response based upon the low energy check pulse; and based, at least partially, upon the detected response, determining to: deliver a high energy laser pulse from the laser fiber to cause a stone to fragment, or deliver another low energy check pulse from the laser fiber.

An example embodiment may be provided in a sheath configured to be removably connected to a shaft of an endoscope. The sheath may comprise a first tube forming a first lumen and an integrally formed second tube forming a second lumen along an exterior side of the first tube. The second tube may have a natural home state comprising a first collapsed configuration against the first tube. The second tube may be resiliently expandable from the first collapsed configuration by fluid to a second expanded configuration, where a laser fiber is able to be inserted into the second lumen when the second tube is in its second expanded configuration. The sheath may comprise a substantially rigid entrance at a proximal end of the second lumen. The entrance may have a general funnel shape. The proximal end of the second lumen may comprise a separate liquid entry into the second lumen.

In an alternate example embodiment the sheath may be insertable through the working channel of the endoscope, and may be removable for disposal. In such an alternate example, the sheath may comprise less than two lumen. The laser fiber may comprise cladding at its front facing surface which protects the laser fiber from damaging the sheath. Another alternate example embodiment may comprise at least one clip for attaching the sheath to the shaft of the endoscope in addition or as an alternative to the first tube.

An example embodiment may be provided in an apparatus comprising an endoscope comprising an image fiber, a laser fiber connected to the endoscope, and a controller configured to control delivery of laser energy from the laser fiber. The controller is configured to control the delivery of laser energy from the laser fiber based, at least partially, upon input into the image fiber at a distal end of the endoscope. The controller may be configured to allow delivery of a low energy check pulse from the laser fiber and, based at least partially upon input into the image fiber at a distal end of the endoscope, control delivery of a high energy laser pulse from the laser fiber to cause a stone to fragment. The controller may also be configured to determine a range between an end of the laser fiber and an object which the low energy check pulse impacts. The controller may be configured to use reflectivity and/or emissivity from the low energy check pulse to control whether or not the high energy laser pulse is emitted from the laser fiber. The controller may be configured to use image processing to controller whether or not the high energy laser pulse is emitted from the laser fiber. The image processing may be configured to recognize at least one of: a shape of at least a portion of the retrieval basket, a color of at least a portion of the retrieval basket, and a pattern on at least a portion of the retrieval basket. The controller may be configured to prevent the high energy laser pulse from being delivered by the laser fiber based upon a determination that the high energy laser pulse would impact a retrieval basket extending out of the distal end of the endoscope. The image processing may be configured to detect at least a portion of the basket device and/or at least a portion of the stone. The controller may be configured to vary the laser energy emitted by the laser fiber, such as frequency and wavelength for example, based upon a determined movement of the stone, such as direction and velocity of the stone relative to the laser fiber. The apparatus may be configured to automatically move, such as rotate, the basket based upon the input into the image fiber. The controller may be configured to adjust delivery of the laser energy and/or move the basket device based upon movement/location of the stone and/or location of the basket device relative to the distal end of the laser fiber. The laser fiber may comprise more than one laser fiber, perhaps configured to deliver different respective energy pulses.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications and variances which fall within the scope of the appended claims.

What is claimed is:

1. A method comprising:
   connecting a sheath to a shaft of an endoscope, where the sheath comprises at least two lumen, where a first one of the lumen is connected to the endoscope with the shaft of the endoscope extending through the first lumen, and where a second one of the lumen is spaced from the shaft of the endoscope providing a channel proximate an exterior side of the shaft;
   inserting a laser fiber into the second lumen; and
   controlling delivery of energy from the laser fiber comprising a low energy check pulse from the laser fiber for detecting a response based upon the low energy check pulse, and a high energy laser pulse from the laser fiber for causing a stone to fragment.

2. A method as in claim 1 further comprising, before inserting the laser fiber into the second lumen, inserting a fluid into the second lumen to expand the second lumen from a collapsed configuration to an expanded configuration.

3. A method as claim 1 further comprising using a range detection system to detect a range between an end of the laser fiber and an object which the low energy check pulse impacts.

4. A method as in claim 1 further comprising using a detection feedback system is configured to:
   measure reflectivity and/or emissivity based upon the low energy check pulse, and/or
   identify an object in front of a path of the low energy check pulse by image processing.

5. A non-transitory program storage device readable by a machine, tangibly embodying a program of instructions executable by the machine for performing operations, the operations comprising:
   delivering a low energy check pulse from a laser fiber;
   detecting a response based upon the low energy check pulse; and
   based, at least partially, upon the detected response, determining to:
     deliver a high energy laser pulse from the laser fiber to cause a stone to fragment, or
     deliver another low energy check pulse from the laser fiber.

6. An apparatus comprising:
   circuitry configured to control delivery of a low energy check pulse from the apparatus;
   circuitry configured to detect a response based upon the low energy check pulse;
   circuitry configured to control delivery of a high energy laser pulse from the apparatus, where the control of the delivery of the high energy laser pulse comprises at least one of:

allowing the high energy laser pulse to be delivered from the apparatus based upon determining that the high energy laser pulse would impact a first predetermined object, or preventing the high energy laser pulse from being delivered from the apparatus based upon determining that the high energy laser pulse would impact a second predetermined object.

7. The apparatus as in claim 6 where the apparatus is configured to detect a range between an end of a laser fiber of the apparatus and the first predetermined object.

8. The apparatus as in claim 6 where the apparatus is configured to measure reflectivity and/or emissivity.

9. The apparatus as in claim 6 where the apparatus is configured to use image processing to determine the first predetermined object and/or the second predetermined object.

10. The apparatus as in claim 6 where the apparatus is configured to recognize at least a portion of the second predetermined object as being a retrieval basket.

11. The apparatus as in claim 6 where the apparatus is configured to recognize the first predetermined object as being a stone.

12. A method comprising:
delivering a low energy check pulse from an apparatus;
detecting a response based upon the low energy check pulse; and
controlling delivery of a high energy laser pulse from the apparatus to cause a stone to fragment, where the controlling of the delivery of the high energy laser pulse from the apparatus prevents the high energy laser pulse from being delivered based upon determining that the high energy laser pulse would impact a retrieval basket.

13. The method of claim 12 where the determining that the high energy laser pulse would impact the retrieval basket comprises recognizing at least one of:
a shape of at least a portion of the retrieval basket,
a color of at least a portion of the retrieval basket, or
a pattern on at least a portion of the retrieval basket.

14. The method of claim 12 further comprising detecting a range between an end of a laser fiber of the apparatus and a location of impact of the low energy check pulse.

15. The method of claim 12 further comprising measuring reflectivity and/or emissivity in the response to the low energy check pulse.

16. The method of claim 12 further comprising using image processing to determine that the high energy laser pulse would impact the retrieval basket.

17. A method comprising:
delivering a low energy check pulse from an apparatus;
detecting a response based upon the low energy check pulse; and
based at least partially upon the detected response, controlling delivery of a high energy laser pulse from the apparatus to cause a stone to fragment, where the controlling of the delivery of the high energy laser pulse comprises determining if a portion of a retrieval basket is located in a path of the high energy laser pulse.

18. The method as in claim 17 where the determining if a portion of the retrieval basket is located in a path of the high energy laser pulse comprises recognizing at least one of:
a shape of at least a portion of the retrieval basket,
a color of at least a portion of the retrieval basket, or
a pattern on at least a portion of the retrieval basket.

19. The method of claim 17 further comprising detecting a range between an end of a laser fiber of the apparatus and a location of impact of the low energy check pulse.

20. The method of claim 17 further comprising measuring reflectivity and/or emissivity in the response to the low energy check pulse.

21. The method of claim 17 further comprising using image processing to determine that the high energy laser pulse would impact the retrieval basket.

* * * * *